United States Patent [19]

Kimura et al.

[11] Patent Number: 4,744,814

[45] Date of Patent: May 17, 1988

[54] N-[(4,6-DIMETHOXYPYRIMIDIN-2-YL)AMINOCARBONYL]-3-TRIFLUOROMETHYLPYRIDINE-2-SULFONAMIDE OR SALTS THEREOF, HERBICIDAL COMPOSITION CONTAINING THE SAME

[75] Inventors: Fumio Kimura; Takahiro Haga; Nobuyuki Sakashita, all of Shiga; Chimoto Honda, Osaka; Kouji Hayashi, Shiga; Toshio Seki, Shiga; Kouji Minamida, Shiga, all of Japan

[73] Assignee: Ishihara Sangyo Kaisha, Osaka, Japan

[21] Appl. No.: 802,279

[22] Filed: Nov. 27, 1985

[30] Foreign Application Priority Data

Dec. 6, 1984 [JP] Japan .................. 59-258186

[51] Int. Cl.$^4$ .................. C07D 401/12; A01N 43/54
[52] U.S. Cl. .................. 71/92; 544/320
[58] Field of Search .................. 544/320; 71/92

[56] References Cited

U.S. PATENT DOCUMENTS

| | | | |
|---|---|---|---|
| 4,301,286 | 11/1981 | Schwing et al. | 544/211 |
| 4,333,760 | 6/1982 | Zimmerman | 71/92 |
| 4,339,267 | 7/1982 | Levitt | 71/92 |
| 4,342,587 | 8/1982 | Levitt | 71/92 |
| 4,372,778 | 2/1983 | Levitt | 71/94 |
| 4,425,155 | 1/1984 | Dumas | 71/93 |
| 4,435,206 | 3/1984 | Levitt | 544/320 |
| 4,456,469 | 6/1984 | Adams, Jr. | 71/93 |
| 4,496,392 | 1/1985 | Levitt | 71/93 |
| 4,518,776 | 5/1985 | Meyer et al. | 544/206 |
| 4,521,597 | 6/1985 | Kristinsson et al. | 544/3 |
| 4,522,645 | 6/1985 | Levitt | 71/93 |
| 4,544,401 | 10/1985 | Levitt | 71/92 |
| 4,549,898 | 10/1985 | Bohner | 71/90 |
| 4,565,567 | 1/1986 | Levitt | 71/92 |
| 4,579,583 | 4/1986 | Fory et al. | 71/92 |
| 4,605,432 | 8/1986 | Adams, Jr. | 71/92 |
| 4,629,494 | 12/1986 | Shapiro | 71/92 |
| 4,629,802 | 12/1986 | Kristinsson et al. | 558/7 |
| 4,643,760 | 2/1987 | Meyer et al. | 71/92 |
| 4,655,823 | 4/1987 | Shapiro | 71/93 |
| 4,657,578 | 4/1987 | Thompson | 71/90 |
| 4,659,361 | 4/1987 | Brown | 71/90 |
| 4,659,369 | 4/1987 | Levitt | 71/92 |
| 4,662,933 | 5/1987 | Thompson | 71/92 |
| 4,666,501 | 5/1987 | Hay et al. | 71/90 |
| 4,666,506 | 5/1987 | Hillemann | 71/90 |
| 4,668,279 | 5/1987 | Rorer | 71/92 |
| 4,668,800 | 5/1987 | Meyer et al. | 549/63 |

FOREIGN PATENT DOCUMENTS 0132230 1/1985 European Pat. Off. .

*Primary Examiner*—John M. Ford
*Attorney, Agent, or Firm*—Sughrue, Mion, Zinn, Macpeak & Seas

[57] ABSTRACT

N-[(4,6-Dimethoxypyrimidin-2-yl)aminocarbonyl]-3-trifluoromethylpyridine-2-sulfonamide or a salt thereof is disclosed. The compound of the invention is useful as a herbicide which has an extremely high herbicidal effect against a wide variety of weeds including strongly noxious weeds but which shows a high safety against tomato and turfs. A process for the production of N-[(4,6-dimethoxypyrimidin-2-yl)aminocarbonyl]-3-trifluoromethylpyridine-2-sulfonamide is also disclosed.

12 Claims, No Drawings

N-[(4,6-DIMETHOXYPYRIMIDIN-2-YL)AMINOCARBONYL]-3-TRIFLUOROMETHYL-PYRIDINE-2-SULFONAMIDE OR SALTS THEREOF, HERBICIDAL COMPOSITION CONTAINING THE SAME

FIELD OF THE INVENTION

The present invention relates to N-[(4,6-dimethoxypyrimidin-2-yl)aminocarbonyl]-3-trifluoromethylpyridine-2-sulfonamide or a salt thereof useful as a herbicide which has an extremely high herbicidal effect against a wide variety of weeds including strongly noxious weeds but which shows a high safety against tomato and turfs.

BACKGROUND OF THE INVENTION

Although N-[(4,6-dimethoxypyrimidin-2-yl)aminocarbonyl]-3-trifluoromethylpyridine-2-sulfonamide of the present invention is included in the substituted pyridinesulfonamide compounds widely expressed by a general formula of U.S. Pat. No. 4,435,206, it is not specifically disclosed in this U.S. patent.

U.S. Pat. No. 4,435,206 describes that N-(heterocyclicaminocarbonyl)pyridinesulfonamides are useful as a herbicide and discloses a number of specific compounds. But only N-[(4,6-dimethylpyrimidin-2-yl)aminocarbonyl]pyridine-2-sulfonamide is proven to have an activity against plants. The herbicidal activity of this compound is, however, still low as compared with that which is expected in practical use. Accordingly, this U.S. patent merely suggests that the N-(heterocyclicaminocarbonyl)pyridinesulfonamides may be used as a herbicide.

In order to develop a herbicide which can kill various noxious weeds at a small dosage, the present inventors have made extensive investigations about the relation between the chemical structure of such types of compounds of U.S. Pat. No. 4,435,206 and biological activity thereof and attained the present invention. That is, it has been found that a compound having an N-[(pyrimidin-2-yl)aminocarbonyl]pyridine-2-sulfonamide skeleton and having a trifluoromethyl group at the 3-position of the pyridine moiety thereof and a methoxy group at each of the 4- and 6-positions of the pyrimidine moiety thereof not only has a high herbicidal activity and a wide herbicidal spectrum as compared with the specific compound of the above-cited U.S. patent, the herbicidal effect of which was confirmed, as well as analogues thereof but also exhibits an excellent herbicidal effect against strongly noxious weeds which are considered to be difficultly controlled, such as purple nutsedge. Further, it has been found that the compound of the present invention is safe against tomato and turfs and can well control weeds which grow in the cultivation field of tomato or turfs, as compared with a number of analogues disclosed in U.S. Pat. No. 4,435,206.

SUMMARY OF THE INVENTION

An object of the present invention is to provide N-[(4,6-dimethoxypyrimidin-2-yl)aminocarbonyl]-3-trifluoromethylpyridine-2-sulfonamide or a salt thereof.

Another object of the present invention is to provide a herbicidal composition containing as an active ingredient N-[(4,6-dimethoxypyrimidin-2-yl)aminocarbonyl]-3-trifluoromethylpyridine-2-sulfonamide or a salt thereof.

A further object of the present invention is to provide a method for controlling noxious weeds by applying N-[(4,6-dimethoxypyrimidin-2-yl)aminocarbonyl]-3-trifluoromethylpyridine-2-sulfonamide or a salt thereof.

An even another object of the present invention is to provide a process for the production of N-[(4,6-dimethoxypyrimidin-2-yl)aminocarbonyl]-3-trifluoromethylpyridine-2-sulfonamide.

An even further object of the present invention is to provide as an intermediate a 3-trifluoromethylpyridine compound represented by the following general formula (I):

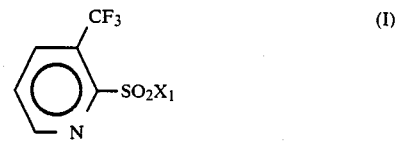

wherein $X_1$ represents a halogen atom, an amino group, an isocyanato group, or a phenoxycarbonylamino group.

DETAILED DESCRIPTION OF THE INVENTION

Examples of salts of N-[(4,6-dimethoxypyrimidin-2-yl)aminocarbonyl]-3-trifluoromethylpyridine-2-sulfonamide according to the present invention include salts of alkali metals such as sodium and potassium, salts of alkaline earth metals such as magnesium and calcium, and salts of amines such as dimethylamine and triethylamine.

The compound of the present invention can be prepared in the following reaction scheme.

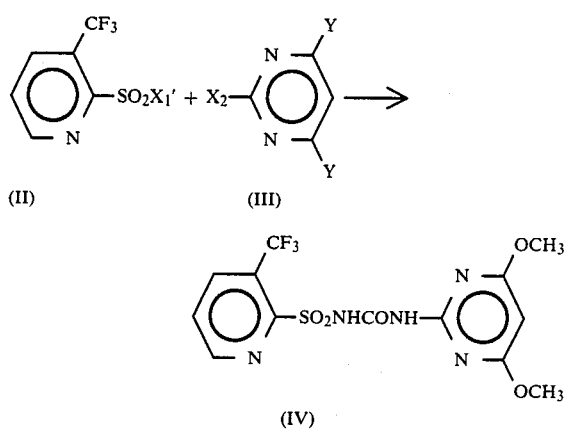

wherein $X_1'$ represents an amino group, an isocyanato group, or a phenoxycarbonylamino group; $X_2$ represents a phenoxycarbonylamino group, an amino group, or an isocyanato group; and Y represents a methoxy group or a halogen atom, provided that when $X_1'$ represents an amino group, then $X_2$ represents a phenoxycarbonylamino group or an isocyanato group; when $X_1'$ represents an isocyanato group or a phenoxycarbonylamino group, then $X_2$ represents an amino group; and that when Y represents a halogen atom, then $X_1'$ represents an amino group and $X_2$ represents an isocyanato group.

In the above reaction, when $X_1'$ represents an amino group, $X_2$ represents an isocyanato group, and Y represents a halogen atom, after the condensation reaction, a conventional methoxylation reaction is carried out.

The compound of the present invention can be specifically synthesized by either one of the following methods [A] to [E].

[A] 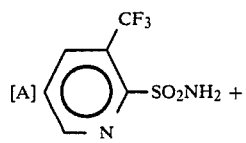
(II')

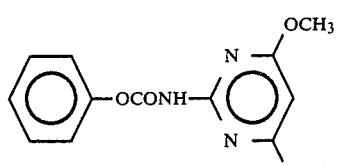
(III')

[B] 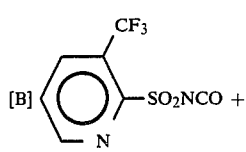
(II")

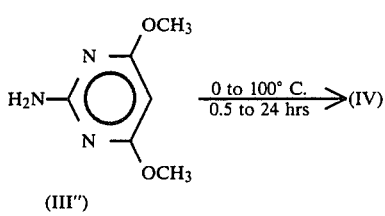
(III")

[C] 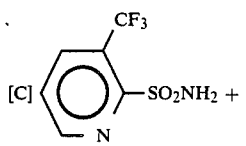
(II')

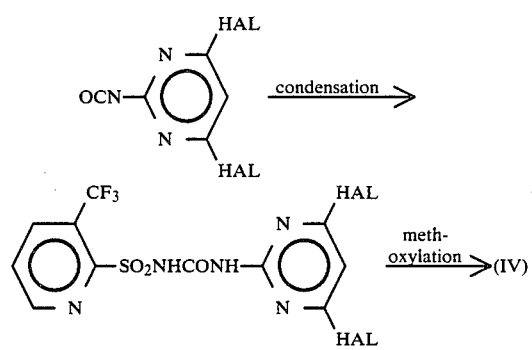

[D] 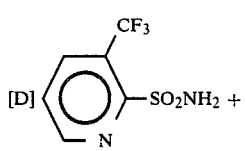
(II')

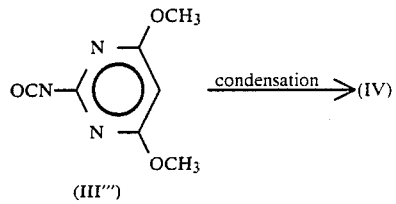
(III''')

[E] 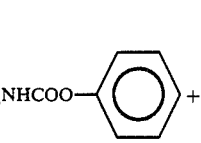
(II''')

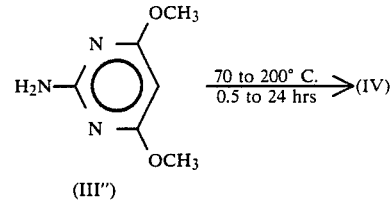
(III")

In the above formulae, HAL means a halogen atom.

The above reactions may be carried out in the presence of a solvent, if desired. Examples of the solvent which can be used include aromatic hydrocarbons such as benzene, toluene, xylene, and chlorobenzene; cyclic or non-cyclic aliphatic hydrocarbons such as chloroform, carbon tetrachloride, methylene chloride, dichloroethane, trichloroethane, hexane, and cyclohexane; ethers such as diethyl ether, methylethyl ether, dioxane, and tetrahydrofuran; nitriles such as acetonitrile, propiononitrile, and acrylonitrile; and aprotic polar solvents such as dimethyl sulfoxide and sulfolane.

The starting compound of the general formula (II) can be prepared by, for example, the following methods.

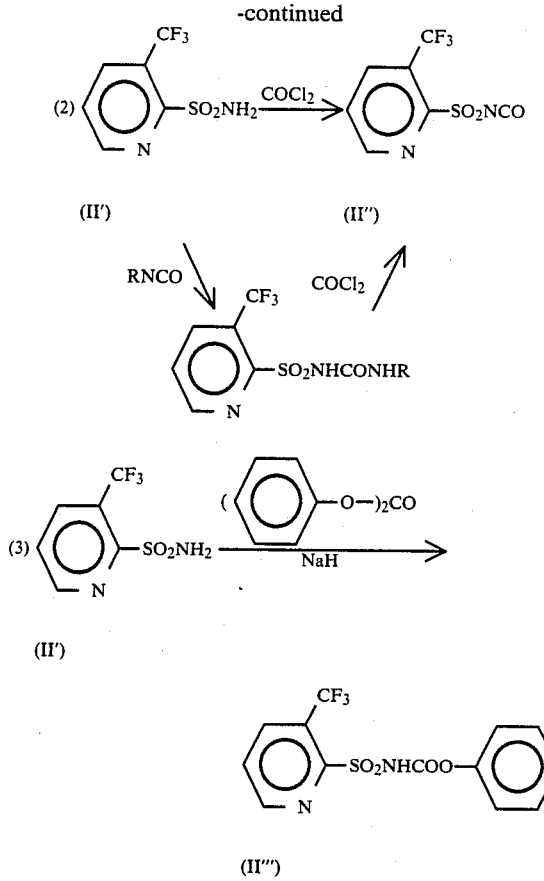

In the above formulae, HAL means a halogen atom, and R represents an alkyl group.

The reaction conditions for preparing the starting compound, such as reaction temperature, reaction time, a solvent which is optionally used, an alkaline substance, etc., can be suitably selected from those of the conventional analogous reactions.

Synthesis examples of N-[(4,6-dimethoxypyrimidin-2-yl)aminocarbonyl]-3-trifluoromethylpyridine-2-sulfonamide are shown below.

SYNTHESIS EXAMPLE 1

[1] 5.0 g of 2-mercapto-3-trifluoromethylpyridine was added to a solution of 25 ml of acetic acid and 50 ml of water, and chlorine gas was passed therethrough under cooling with salt-ice at $-10°$ C. or lower for 30 minutes. 50 ml of water was added thereto, and a crystal of precipitated 3-trifluromethylpyridine-2-sulfonyl chloride (m.p.: 56°–59° C.) was filtered off and dried.

Thereafter, the thus-obtained crystal was added to 50 ml of a 28% aqueous ammonia solution under cooling with ice, and the mixture was reacted with stirring for 2 hours.

After completion of the reaction, the reaction mixture was washed with ethyl acetate, and the aqueous ammonia solution was distilled off under reduced pressure to obtain a crystal. This crystal was filtered off, washed with water, and then dried to obtain 2.35 g of 3-trifluoromethylpyridine-2-sulfonamide having a melting point of 135° to 140° C.

[2] To a solution of 120 mg of 3-trifluoromethylpyridine-2-sulfonamide obtained in [1] above and 150 mg of 2-phenoxycarbonylamino-4,6-dimethoxypyrimidine in 1 ml of anhydrous acetonitrile was added 83 mg of 1,5-diazabicyclo[5,4,0]-5-nonen dissolved in 1 ml of anhydrous acetonitrile with stirring at room temperature, and the mixture was reacted for 1.5 hours.

After completion of the reaction, the reaction mixture was poured into 50 ml of ice water, made weakly acidic with concentrated hydrochloric acid, and then allowed to stand for 2 hours. A precipitated crystal was filtered off and dried to obtain 130 mg of a desired product having a melting point of 154° to 159° C.

SYNTHESIS EXAMPLE 2

[1] 0.354 g of sodium hydride (purity: 60%) was added to 5 ml of dimethylformamide, and a solution of 2.0 g of 3-trifluoromethylpyridine-2-sulfonamide in 10 ml of dimethylformamide was added dropwise thereto with stirring under cooling with ice. A solution of 1.89 g of diphenyl carbonate in 10 ml of dimethylformamide was then added dropwise thereto. Thereafter, the mixture was reacted with stirring at room temperature for 3 days.

After completion of the reaction, the reaction mixture was added to a mixed solution of 50 ml of dilute hydrochloric acid and 50 ml of ethyl acetate. The ethyl acetate layer was separated, washed with water, and dried over anhydrous sodium sulfate, and the ethyl acetate was distilled off under reduced pressure to obtain a residue. This residue was recrystallized from a mixed solvent of diethyl ether and n-hexane to obtain 1.63 g of N-phenoxycarbonyl-3-trifluoromethylpyridine-2-sulfonamide having a melting point of 130° to 133.5° C.

[2] 0.5 g of N-phenoxycarbonyl-3-trifluoromethyl-pyridine-2-sulfonamide and 0.286 g of 2-amino-4,6-dimethoxypyrimidine were added to 10 ml of dioxane, and the mixture was reacted with stirring at 100° C. for one hour.

After completion of the reaction, the reaction mixture was stood for cooling and poured into water. A precipitated crystal was filtered off and dried to obtain 0.42 g of a desired product.

A 3-trifluoromethylpyridine compound represented by the general formula (I):

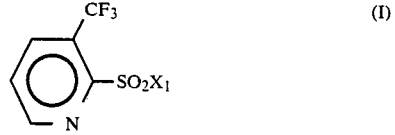

wherein $X_1$ represents a halogen atom, an amino group, an isocyanato group, or a phenoxycarbonylamino group, is considered to be a novel compound.

The 3-trifluoromethylpyridine compound of the general formula (I) which can be used as an intermediate can be derived into N-[(4,6-dimethoxypyrimidin-2-yl)aminocarbonyl]-3-trifluoromethylpyridine-2-sulfonamide, and it is useful because the thus-derived compound exhibits a high herbicidal activity as demonstrated in the test examples described hereunder.

The compound of the present invention can control a wide variety of weeds such as Cyperaceae, e.g., rice flatsedge (*Cyperus iria* L.), purple nutsedge (*Cyperus rotundus* L.), and *Cyperus brevitolius* HASSK.; Leguminosae, e.g., white clover (*Trifolium repens* L.), narrowleaf vetch (*Vicia sativa* L.), and sicklepod (*Cassia tora* L.); Oxalidaceae, e.g., creeping woodsorrel (*Oxalis*

*corniculata* L.) and pink woodsorrel (*Oxalis martiana* ZUCC.); Compositae, e.g., common cocklebur (*Xanthium strumarium* L.), annual fleabane (*Erigeron annuus* L.), common mugwort (*Artemisia vulgaris* L.), and broadleaved fleabane (*Erigeron sumatrensis* RETZ.); Polygonaceae, e.g., green smartweed (*Polygonum lapathifolium* L.) and broadleaf dock (*Rumex japonicus* HOUTTUYN); Gramineae, e.g., large crabgrass (*Digitaria adscendens* HENR.), common barnyard-grass (*Echinochloa crus-galli* L.), quackgrass (*Agropyron repens* L.), and wild oat (*Avena fatua* L.); Amaranthaceae, e.g., slender amaranth (*Amaranthus viridis* L.) and livid amaranth (*Amaranthus lividus* L.); Chenopodiaceae, e.g., common lambsquarters (*Chenopodium album* L.); Caryophyllaceae, e.g., common chickweed (*Stellaria media* CRY.) and startwort (*Stellaria alsine* GRIMM.); Convolvulaceae, e.g., common morningglory (*Pharbitis purpurea* VOIGT.); and Portulacaceae, e.g., common purslane (*Portulaca oleracea* L.).

Herbicides containing the compound according to the present invention as the active ingredient will find many other applications such as agricultural fields, e.g., upland farms, orchards, and mulberry fields and non-agricultural fields, e.g., forests, farm roads, playgrounds, factory sites, and turf fields.

In particular, the compound of the present invention does not damage warm-season turfs such as Zoysia sp., e.g., *Zoysia japonia* and *Zoysia metrella* and Cymodon sp., e.g., tifton and common bermuda grass and is safe against tomato, and therefore, it is very useful.

Almost all of conventional herbicides used in the turf field have an effect only against broad-leaved weeds, and no chemicals can simultaneously control a wide range of weeds including strongly noxious weeds such as Cyperaceae and Gramineae. Accordingly, the compound of the present invention is very useful.

When a herbicidal composition of the present invention is applied, the herbicidal compound of the present invention is usually formulated into various forms such as granules, dust, wettable powder, or water-soluble powder by optionally incorporating conventional agriculturally acceptable adjuvants, for example, a carrier, diluent, solvent, spreader, or surfactant. A suitable mixing ratio of the active ingredient to the adjuvant(s) ranges from 0.5:99.5 to 90:10 by weight and preferably from 1:99 to 60:40 by weight. An optimum amount of the active ingredient applied cannot be unequivocally defined because it varies according to various factors such as the climate condition, the weather condition, the soil condition, the form of the chemical, the type of weeds to be controlled, or the time of application, but the amount of the active ingredient is usually from 0.01 to 100 g per are (100 m$^2$) and preferably from 0.1 to 10 g per are.

The herbicidal composition of the present invention can be applied by soil treatment or foliar treatment.

The herbicidal composition of the present invention can be mixed or used together with other agricultural chemicals, fertilizers, soil, or safeners. Sometimes, such a conjoint use brings about a more excellent effect or action. Examples of other herbicides which can be mixed with the herbicidal composition of the present invention are listed below.

Potassium 4-amino-3,5,6-trichloro-2-pyridincarboxylate
Ethyl 2,4-dichlorophenoxyacetate
Ethyl 2-methyl-4-chlorophenoxyacetate
4-Amino-6-tert-butyl-3-(methylthio)-1,2,4-triazin-5(4H)-one
2-(2-Chloro-4-ethylamino-s-triazin-6-ylamino)-2-methylpropionitrile
2-Chloro-4,6-bis(ethylamino)-s-triazine
2-Chloro-4-ethylamino-6-isopropylamino-s-triazine
N'-[5-(1,1-Dimethylethyl)-3-isoxazol]-N,N-dimethylurea
3-(3,4-Dichlorophenyl)-1,1-dimethylurea
3-(3,4-Dichlorophenyl)-1-methoxy-1-methylurea
3,5-Dinitro-N',N'-dipropylsulfanylamide
2-Methylthio-4-ethylamino-6-isopropylamino-s-triazine
n-Butyl α-[4-(5-trifluoromethyl-2-pyridyloxy)phenoxy]propionate
Methyl α-[4-(2,4-dichlorophenoxy)phenoxy]propionate
Methyl α-[4-(3-chloro-5-trifluoromethyl-2-pyridyloxy)phenoxy]propionate
2-[1-(Ethoxyimino)-butyl]-5-(2-ethylthiopropyl)-3-hydroxy-2-cyclohexen-1-one
1,1'-Dimethyl-4,4'-bipyridylium dichloride and isopropylamine salt of N-(phosphonomethyl)glycine
Sodium N'-methoxycarbonylsulfanylamide
Sodium 2,2-dichloropropionate
3,4-Dichloropropionanilide
1,2-Dimethyl-3,5-diphenyl-1H-pyrazolium methylsulfate
Ethyl N-benzoyl-N-(3-chloro-4-fluorophenyl)-2-aminopropionate
3,4-Dimethyl-2,6-dinitro-N-(1-ethyl)propylaniline
α,α,α-Trifluoro-2,6-dinitro-N,N-dipropyl-p-toluidine
2-Chloro-2',6'-diethyl-N-(methoxymethyl)acetanilide
2-Chloro-N-(2-ethyl-6-methylphenyl)-N-(2-methoxy-1-methylethyl)acetamide
5'-(Trifluoromethanesulfonamido)aceto-2'4'-xylidide
2-Chloro-N-isopropylacetanilide
3,5-Dibromo-4-hydroxybenzonitrile
3,5-Diiodo-4-octanoyloxybenzonitrile
4-Chlorobutyn-2-yl-N-(3-chlorophenyl)carbamate Some typical formulation examples of the herbicidal composition of the present invention are shown below.

|     |                                                                                                                                                           | parts by weight |
| --- | --------------------------------------------------------------------------------------------------------------------------------------------------------- | --------------- |
| (1) | Newlite (trade name of Nippon Taikagenryo Co., Ltd.)                                                                                                      | 97              |
| (2) | Dikssol W-92 (trade name of Dai-ichi Kogyo Seiyaku Co., Ltd.)                                                                                             | 2               |
| (3) | N—[(4,6-Dimethoxypyrimidin-2-yl)aminocarbonyl]-3-trifluoromethylpyridine-2-sulfonamide (hereinafter abbreviated as "compound of the invention")           | 1               |

The ingredients (1) to (3) are mixed and pulverized to form a dust.

FORMULATION EXAMPLE 2

|     |                                                                                                   | parts by weight |
| --- | ------------------------------------------------------------------------------------------------- | --------------- |
| (1) | Water-soluble starch                                                                              | 75              |
| (2) | Sodium ligninsulfonate                                                                            | 5               |
| (3) | Sodium salt of N—[(4,6-dimethoxypyrimidin-2-yl)-aminocarbonyl]-3-trifluoromethylpyridine-2-sulfonamide | 20              |

The ingredients (1) to (3) are mixed to form a water-soluble powder.

FORMULATION EXAMPLE 3

| | | parts by weight |
|---|---|---|
| (1) | Jeeklite (trade name for kaolinite, produced by Jeeklite Co., Ltd.) | 78 |
| (2) | Lavelin S (trade name of Dai-ichi Kogyo Seiyaku Co., Ltd.) | 2 |
| (3) | Sorpol 5039 (trade name of Toho Chemical Co., Ltd.) | 5 |
| (4) | Carplex (trade name of Shionogi & Co., Ltd.) | 15 |

A mixture of the ingredients (1) to (4) and the compound of the invention are mixed in a weight ratio of 4:1 to form a wettable powder.

FORMULATION EXAMPLE 4

| | | parts by weight |
|---|---|---|
| (1) | Diatomaceous earth | 92.5 |
| (2) | Dikssol W-66 (trade name of Dai-icho Kogyo Seiyaku Co., Ltd.) | 5 |
| (3) | Dikssol W-09B (trade name of Dai-ichi Kogyo Seiyaku Co., Ltd.) | 2 |
| (4) | Compound of the invention | 0.5 |

The ingredients (1) to (4) are mixed to form a wettable powder.

FORMULATION EXAMPLE 5

| | | parts by weight |
|---|---|---|
| (1) | Hi-Filler No. 10 (trade name of Matsumura Sangyo Co., Ltd.) | 33 |
| (2) | Sorpol 5050 (trade name of Toho Chemical Co., Ltd.) | 3 |
| (3) | Sorpol 5073 (trade name of Toho Chemical Co., Ltd.) | 4 |
| (4) | Compound of the invention | 60 |

The ingredients (1) to (4) are mixed to form a wettable powder.

The herbicidal activity testing of the compound of the present invention and results obtained are shown below.

The test compounds used in the test examples are shown in Table 1.

TABLE 1

| Compound No. | Compound |
|---|---|
| 1 | 3-CF$_3$, 2-pyridyl-SO$_2$NHCONH-(4,6-di-OCH$_3$ pyrimidinyl) |
| 2 | 3-CF$_3$, 2-pyridyl-SO$_2$NHCONH-(4-OCH$_3$, 6-N, pyrimidinyl type) |
| 3 | 3-CF$_3$, 2-pyridyl-SO$_2$NHCONH-(4,6-di-CH$_3$ pyrimidinyl) |
| 4 | 3-CF$_3$, 2-pyridyl-SO$_2$NHCONH-(4-CH$_3$, 6-OCH$_3$ pyrimidinyl) |
| 5 | 2-pyridyl-SO$_2$NHCONH-(4,6-di-OCH$_3$ pyrimidinyl) |
| 6 | 2-pyridyl-SO$_2$NHCONH-(4,6-di-OCH$_3$ triazinyl) |
| 7 | 2-pyridyl-SO$_2$NHCONH-(4,6-di-CH$_3$ pyrimidinyl) |
| 8 | 3-Cl, 2-pyridyl-SO$_2$NHCONH-(4,6-di-OCH$_3$ pyrimidinyl) |
| 9 | 3-COOCH$_3$, phenyl-SO$_2$NHCONH-(4,6-di-OCH$_3$ pyrimidinyl) |

Compound No. 1: according to the present invention
Compound Nos. 2 & 3: comparison compounds included in Formula I of U.S. Pat. No. 4,435,206
Compound Nos. 4 to 9: comparison compounds specifically disclosed in U.S. Pat. No. 4,435,206

TEST EXAMPLE 1

Each 1/10,000 are (1/100 m$^2$) pot was charged with upland soil, and predetermined amounts of seeds of various test plants were sown. When the test plants had respectively reached the prescribed growth stage as set forth below, an aqueous dispersion prepared by diluting a wettable powder containing a predetermined amount of each of the test compounds shown in Table 2 with 5 l/are of water was foliarly applied on the plant by means of a small-sized sprayer. Thirty days after the application, the degree of growth of the plant was visually observed. The results are shown in Table 2. The weed control shown in Table 2 was evaluated on a scale of 10 grades in which 10 indicates that the plant was completely killed and 1 indicates one the same as untreated check.

| A: | common cocklebur | 2-leaf stage |
|----|------------------|--------------|
| B: | common morningglory | 2-leaf stage |
| C: | green smartweed | 4-leaf stage |
| D: | sicklepod | 1-leaf stage |
| E: | wild oat | 2-leaf stage |
| F: | barnyardgrass | 2-leaf stage |
| G: | large crabgrass | 2-leaf stage |

TABLE 2

| Compound No. | Rate of Active Ingredient (g/are) | Weed Control | | | | | | |
|---|---|---|---|---|---|---|---|---|
| | | A | B | C | D | E | F | G |
| 1 | 2 | 10 | 10 | 10 | 10 | 10 | 10 | 10 |
|   | 1 | 10 | 10 | 10 | 10 | 10 | 10 | 10 |
|   | 0.5 | 10 | 10 | 10 | 10 | 10 | 10 | 10 |
| 7 | 2 | 4 | 1 | 2 | 1 | 1 | 1 | 1 |
|   | 1 | 3 | 1 | 1 | 1 | 1 | 1 | 1 |
|   | 0.5 | 1 | 1 | 1 | 1 | 1 | 1 | 1 |

TEST EXAMPLE 2

The same procedures as in Test Example 1 were repeated except that the test plants were changed to sicklepod (1-leaf stage), large crabgrass (2-leaf stage), and purple nutsedge (5- to 6-leaf stage) and that the rate of the active ingredient was changed as shown in Table 3. The results are shown in Table 3.

TABLE 3

| Compound No. | Rate of Active Ingredient (g/are) | Weed Control | | |
|---|---|---|---|---|
| | | Sicklepod | Large crabgrass | Purple nutsedge |
| 1 | 0.5 | 8 | 9 | 9 |
| 3 | 2 | 3 | 8 | 5 |
| 4 | 0.5 | 4 | 4 | 2 |
| 7 | 0.5 | 1 | 1 | 1 |

TEST EXAMPLE 3

In Test Example 1, germinated tubers of purple nutsedge were planted in a pot, and when the purple nutsedge had reached a 4-leaf stage, the same treatment as in Test Example 1 was carried out. The results are shown in Table 4.

TABLE 4

| Compound No. | Weed Control against Purple Nutsedge Rate of Active Ingredient (g/are) | | |
|---|---|---|---|
| | 1 | 0.5 | 0.25 |
| 1 | 10 | 10 | 10 |
| 2 | 2 | 1 | 1 |
| 3 | 1 | 1 | 1 |
| 4 | 2 | 1 | 1 |
| 5 | 4 | 3 | 2 |
| 6 | 1 | 1 | 1 |
| 7 | 1 | 1 | 1 |

TEST EXAMPLE 4

Mats of *Zoysia metrella* were sodded in a 1/2,000 are (1/20 m$^2$) pot and mowed about 4 times every two weeks. Seedings of tomato of 4-leaf stage were transplanted in a 1/2,000 are (1/20 m$^2$) pot. When the tomato had reached a 8-leaf stage, an aqueous dispersion prepared by diluting a wettable powder containing a predetermined amount of each of the test compounds shown in Table 5 with 5 l/are of water was foliarly applied on the plant by means of a small-sized sprayer. The degree of growth of the plant was visually observed 35 days after the application for *Zoysia metrella* and 25 days after the application for tomato, respectively. The degree of growth was evaluated on a scale of 10 grades in the same manner as in Test Example 1. The results are shown in Table 5.

TABLE 5

| Compound No. | Degree of Growth | | | | |
|---|---|---|---|---|---|
| | *Zoysia metrella* Rate of Active Ingredient (g/are) | | | Tomato Rate of Active Ingredient (g/are) | |
| | 5 | 2.5 | 1.25 | 2.5 | 1.25 |
| 1 | 1 | 1 | 1 | 1 | 1 |
| 9 | 6 | 5 | 4 | 8 | 9 |

TEST EXAMPLE 5

Seedings of *Zoysia metrella* were sodded in a 1/2,000 are (1/20 m$^2$) pot and mowed about 4 times every two weeks. Thereafter, tubers of purple nutsedge were sodded in the pot. When the purple nutsedge had reached a 6-leaf stage, the same procedures as in Test Example 1 were repeated. The results are shown in Table 6.

TABLE 6

| Compound No. | Turf Injury *Zoysia metrella* Rate of Active Ingredient (g/are) | Weed Control Purple Nutsedge Rate of Active Ingredient (g/are) | |
|---|---|---|---|
| | 2.5 | 4 | 1 |
| 1 | 1 | 10 | 10 |
| 8 | 4 | 9 | 6 |
| 9 | 5 | 10 | 10 |

While the invention has been described in detail and with reference to specific embodiments thereof, it will be apparent to one skilled in the art that various changes and modifications can be made therein without departing from the spirit and scope thereof.

What is claimed is:

1. A herbicidal composition comprising, as an active ingredient, N--[(4,6-Dimethoxyprimidin-2-yl)amino-carbonyl]-3-trifluoromethylpyridine-2-sulfonamide or a salt thereof in a herbicidally effective amount sufficient for control of at least one noxious weed of the group consisting of Cyperaceae, Leguminosae, Oxalidaceae, Polygonaceae, Gramineae, Amaranthaceae, Chenopodiaceae, Caryophyllaceae, Compositae, Convolvulaceae and Portulacaceae, and an agriculturally acceptable adjuvant.

2. A herbicidal composition as claimed in claim 1, wherein the mixing ratio of said N-[(4,6-dimethoxypyrimidin-2-yl)aminocarbonyl]-3-trifluoromethylpyridine-2-sulfonamide or salt thereof to said agriculturally acceptable adjuvant is from 0.5:99.5 to 90:10 by weight.

3. A herbicidal composition as claimed in claim 1, wherein the amount of said compound or salt thereof does not damage warm-season turf or tomato.

4. A method for controlling at least one noxious weed of the group consisting of Cyperaceae, Leguminosae, Oxalidaceae, Polygonaceae, Gramineae, Chenopodiaceae, Caryophyllaceae, Compositae, Convolvulaceae and Portulacaceae which comprising applying a herbicidally effective amount of N-[(4,6-dimethoxypyrimidin-2-yl)aminocarbonyl]-3-trifluoro-methylpyridine-2-sulfonamide or a salt thereof sufficient to control said at least one noxious weed to a locus to be protected.

5. A method as claimed in claim 4, wherein the herbicidally effective amount is from 0.01 to 100 g/are.

6. A method as claimed in claim 4, wherein the locus to be protected is a locus where a turf is grown.

7. A method as claimed in claim 6, wherein said turf is a warm-season turf.

8. A method as claimed in claim 4, wherein the locus to be protected is a locus where tomato is grown.

9. A method as claimed in claim 7, wherein said turf is Zoysia sp. or Cynodon sp.

10. A method as claimed in claim 4, wherein said locus is a turf field.

11. A method as claimed in claim 4, wherein said locus is a non-agricultural field.

12. N-[(4,6-Dimethoxypyrimidin-2-yl)aminocarbonyl]-3-trifluoromethylpyridine-2-sulfonamide or a salt thereof.

* * * * *